(12) United States Patent
Chong et al.

(10) Patent No.: US 9,107,441 B2
(45) Date of Patent: Aug. 18, 2015

(54) COMPOSITION FOR REDUCING ABSORPTION OF DIETARY FAT

(75) Inventors: Pee Win Chong, Petaling Jaya Selangor (MY); Thomas Hafner, Kuala Lumpur (DE); Istvan Puskas, Hungary (HU)

(73) Assignee: INQPHARM GROUP SDN. BHD., Kuala Lumpur (MY)

( * ) Notice: Subject to any disclaimer, the term of this patent is extended or adjusted under 35 U.S.C. 154(b) by 0 days.

(21) Appl. No.: 13/697,503

(22) PCT Filed: May 13, 2011

(86) PCT No.: PCT/MY2011/000044
§ 371 (c)(1),
(2), (4) Date: Nov. 12, 2012

(87) PCT Pub. No.: WO2011/142652
PCT Pub. Date: Nov. 17, 2011

(65) Prior Publication Data
US 2013/0059817 A1 Mar. 7, 2013

Related U.S. Application Data

(60) Provisional application No. 61/389,732, filed on Oct. 5, 2010.

(30) Foreign Application Priority Data

May 14, 2010 (MY) .......................... PI 2010002277

(51) Int. Cl.
| | | |
|---|---|---|
| *A61K 31/722* | (2006.01) | |
| *A61K 31/724* | (2006.01) | |
| *A61K 31/732* | (2006.01) | |
| *A61K 36/33* | (2006.01) | |
| *A61P 3/00* | (2006.01) | |
| *A61P 3/04* | (2006.01) | |
| *A61P 3/06* | (2006.01) | |
| *A23L 1/308* | (2006.01) | |
| *A61K 31/715* | (2006.01) | |

(52) U.S. Cl.
CPC .............. *A23L 1/308* (2013.01); *A23L 1/3081* (2013.01); *A23L 1/3082* (2013.01); *A23L 1/3085* (2013.01); *A61K 31/722* (2013.01); *A61K 31/724* (2013.01); *A61K 31/732* (2013.01); *A61K 36/33* (2013.01); *A23V 2002/00* (2013.01); *A61K 31/715* (2013.01)

(58) Field of Classification Search
None
See application file for complete search history.

(56) References Cited

U.S. PATENT DOCUMENTS

| | | | |
|---|---|---|---|
| 2003/0092673 A1* | 5/2003 | Struszczyk et al. ............. | 514/55 |
| 2004/0126444 A1 | 7/2004 | D'Huart | |
| 2004/0142903 A1* | 7/2004 | Femia et al. ..................... | 514/58 |
| 2005/0215523 A1* | 9/2005 | Lai et al. ......................... | 514/58 |
| 2006/0189574 A1* | 8/2006 | Hadvary et al. ................. | 514/58 |

FOREIGN PATENT DOCUMENTS

| | | |
|---|---|---|
| EP | 1377183 B1 | 1/2004 |
| JP | 2987581 B1 | 12/1999 |
| WO | WO 01/32038 A1 | 5/2001 |
| WO | WO 03/105600 A1 | 12/2003 |
| WO | WO 2004/054383 A1 | 7/2004 |
| WO | WO 2006/004574 A2 | 1/2006 |

OTHER PUBLICATIONS

Galati, E. et al Biological activity of *Opuntia ficus* indica cladodes . . . Pharm. Biol. (2003) vol. 41, No. 3, pp. 175-179.*
Maestrelli, F. et al "A new drug nanocarrier . . . " Eur. J. Pharm. Biopharm. (2006) vol. 63, pp. 79-86.*
Machine translation of JP 2007-284366 (2007).*
Machine translation of KR 2007-0112319 (2007).*
Lina, B. et al "Subchronic oral toxicity studies with gamma-cyclodextrins . . . " Reg. Tox. Pharm. (1998) vol. 27, pp. 178-188.*
Lina, B. et al "Subchronic oral toxicity studies with gamma-cyclodextrins . . . " Reg. Tox. Pharm. (2004) vol. 39, pp. S14-S26.*
Machine translation of JP 2000-069939 (2000).*
Heck et al "Orlistat, a new lipase inhibitor for the management of obesity" Pharmacotherapy 20, 2000, pp. 270-279, abstract only.
US Food and Drug Administration press release Aug. 24, 2009.
M.D. Gades & J.S.Stern, "Chitosan Supplementation and Fecal Fat Excretion in Men", Obesity Research 11, 2003, pp. 683-688.
Fernandez et al, Journal of Nutrition 1990, 120 (pp. 1283-1290).
Fernandez et al, Journal of Nutrition 1992, 122 (pp. 2330-2340).
Fernandez et al, Journal of Nutrition 1994, 124 (pp. 817-824).
Remington's Pharmaceutical Sciences, 20th Edition, Williams & Wilkins, Pennsylvania USA, (2000) table of contents only.
Cyclodextrin Technology, J. Szejtli, Kluwer Ed. Dordrecht, Holland, 1988, p. 1 only.
Goycoolea F.M. & A.Cardenas, "Pectins from *Opuntia* spp: a short review", J. PACD, 2003 (pp. 17-19).
Database Caplus (Online), Chemical Abstracts Service, XP000002657261, Database accession No. 2004:316666 (Abstract), (2003).
Database Caplus (Online), Chemical Abstracts Service, XP000002657262, Database accession No. 2009:1504185 abstract & JP 7 008223 A, (1995).
Database WPI, Week 200343, Thomson Scientific, AN 2003-451686, XP000002657263 & JP 2002 371001 A, (2003).

(Continued)

*Primary Examiner* — Leigh Maier
(74) *Attorney, Agent, or Firm* — Lathrop & Gage LLP; James H. Velema, Esq.

(57) ABSTRACT

This invention relates to compositions for reducing the absorption or bioavailability of lipids in the gastrointestinal tract, and to methods for the preparation and use of these compositions. The compositions comprise a source of dietary fiber together with a cyclodextrin. The compositions of the invention are suitable for use in the prevention and treatment of obesity or hyperlipidaemia.

16 Claims, 4 Drawing Sheets

(56) References Cited

OTHER PUBLICATIONS

Derwent, "Edible Fibre-rich diet food—comprises formed corn food contg. alpha cellulose, beta cyclodextrin, pectin, guar gum, algin and salt" 1996, XP002253814 (Abstract), JP 7-298854 A.

Database Caplus (Online), Chemical Abstracts Service, XP000002657264, Database accession No. 2009:1483643 abstract & JP 3 139266 A, (1991).

Database Caplus (Online), Chemical Abstracts Service, XP000002657265, Database accession No. 2005:1235680 abstract & CN 1 596 742 A, (2005).

Database Caplus (Online), Chemical Abstracts Service, XP000002657266, Database accession No. 2006:395566 abstract & CN 1 759 748 A, (2006).

Database WPI, Week 201032, Thomson Scientific, AN 2010-D54832, XP000002657267 & CN 101 669 578 A, (2010).

Database Caplus (Online), Chemical Abstracts Service, XP000002657270, Database accession No. 2010:386578 (Abstract), (2008).

Database WPI, Week 200835, Thomson Scientific, AN 2008-F24549, XP000002657271 & KR 2007 0112319 A (Abstract), (2007).

Database WPI, Week 201127, Thomson Scientific, AN 2011-D03984, XP000002657268 & CN 101 953 390 A, (2011).

CRC Handbook of Dietary Fiber in Human Nutrition, 3rd Edition, CRC Press, 2001. pp. 9-10 (Chapter 2.1—Definitions of Dietary Fiber—G. Spiller).

CRC Handbook of Dietary Fiber in Human Nutrition, 3rd Edition, CRC Press, 2001. pp. 257-269 (Chapter 4.6—Influences of Fiber on the Ecology of Intestinal Flora—M. N. Woods & S.L. Gorbach).

National Center for Complementary and Alternative Medicine (NCCAM), NCCAM Interim Policy: Biologically Active Agents Used in Complementary and Alternative Medicine (CAM) and Placebo Materials, 2005: NOT-AT-05-003.

"Position of the American Dietetic Association: Health Implications of Dietary Fiber", Journal of the American Dietetic Association 2008, vol. 108: pp. 1716-1731.

Lee et al, "Antihyperlipidemic Effect of Crocin Isolated from the Fructus of *Gardenia jasminoides* and its Metabolite Cocetin", Biological & Pharmaceutical Bulletin, 2005, 28(11), pp. 2106-2110.

Database WPI, Week 198527, Thomson Scientific, AN 1985-163264 & JP 60 094912 A, (1985).

Database Medline, AN NLM16423626 Feb. 2006.

Database WPI, Week 200781, Thomson Scientific, AN 2007-877977 & JP 2007 284366 A, (2007).

International Search Report from PCT/MY2011/000044 dated Aug. 22, 2011.

Response to the Written Opinion of the ISA/Art 34 Amendments from PCT/MY2011/000044 dated Mar. 12, 2012.

International Preliminary Report on Patentability from PCT/MY2011/000044 dated Oct. 12, 2012.

Rule 161 Communication issued under European Regional Phase Application 1727807.7, Jan. 9, 2013.

\* cited by examiner

COMPOSITION FOR REDUCING ABSORPTION OF DIETARY FAT

RELATED APPLICATIONS

This application is a 35 U.S.C. §371 filing of International Application No. PCT/MY2011/000044 filed May 14, 2011, which claims priority to Malaysian Patent Application No: PI2010002277, filed 14 May 2010 and U.S. Patent Application No. 61/389,732, filed Oct. 5, 2010. The entire contents of each of the above documents are incorporated herein by reference.

FIELD OF THE INVENTION

This invention relates to a composition for reducing fat absorption in the gastrointestinal tract, and to method for the preparation and use of this composition. The composition comprises a source of dietary fibre together with a cyclodextrin.

BACKGROUND OF THE INVENTION

There is a clear relationship between weight gain, obesity and a number of common pathological and metabolic disorders, including diabetes, insulin resistance, metabolic syndrome, cardiovascular disease, hypertension, atherosclerosis, and elevated blood lipid levels. Due to the increasing prevalence of overweight and obesity in the global population, body weight management has become a key element of modern healthcare, and more effective means of weight reduction are urgently needed.

Overweight and obesity result from a level of energy intake which exceeds the body's energy expenditure. Reduction of body weight may be achieved via reducing total caloric intake from the diet, or by reducing caloric intake contributed by specific dietary components. For example, caloric intake can be reduced via control of dietary fat consumption or via control of fat absorption in vivo. Because of its role in the pathogenesis of cardiovascular disease, control of fat intake is particularly important.

Lifestyle changes are very difficult to implement, and as physical activity in the developed world continues to decline and Western-style diets are adopted by developing countries, the prevalence of obesity and its associated health problems is expected to increase world-wide. However, the effectiveness of currently-available drugs and supplements for promoting weight control or weight loss is very variable, particularly if they are not used in conjunction with a calorie-restricted diet plus an exercise regimen.

Currently there are two US Food and Drug Administration-approved anti-obesity drugs, Orlistat and Sibutramine. Orlistat, marketed under the names Xenical and Alli, inhibits pancreatic lipase activity in the small intestine. Pancreatic lipase breaks down triglycerides into fatty acids and monoglycerides, which are subsequently absorbed into the body. Thus inhibition of lipase activity effectively reduces fat absorption. A reduced fat diet is recommended while taking this medication. In the absence of major dietary changes, the adverse effects of gastrointestinal discomfort, diarrhea and flatulence have limited its use. (See Heck et al.: Orlistat, a new lipase inhibitor for the management of obesity, Pharmacotherapy 20:270-279. 2000). There have also been 32 reports of severe liver damage, including 6 cases of liver failure, in patients taking this agent between 1999 and 2008 (US Food and Drug Administration press release 24 Aug. 2009). Sibutramine, marketed under the names Meridia and Reductil, is a serotonin and norepinephrine reuptake inhibitor, and reduces body weight by suppressing appetite. It has significant side effects, such as hypertension, and life-style modifications, such as a reduced fat diet, are also recommended for patients taking this agent.

Because of the side-effect profiles and limited efficacy of these approved agents, additional effective agents with no or minimum side-effects are urgently needed in the art.

Chitosan, which is obtained from the shells of crustaceans, may "trap" or absorb large quantities of fat and thereby inhibits intestinal fat absorption. Its activity is at least to some extent dependent on pH and lipid type.

The anti-hyperlipidaemic effects of a number of plant fibre-containing materials, such as pectin, corn fibre, beta-glucan, guar gum, gum acacia, psyllium, glucomannan, and the like, have long been known. The main fat-binding constituent of these plant materials, regardless of the specific plant origin, is an ionic polysaccharide called pectin. Pectin is a natural part of the human diet, being found in plant cell walls, but does not contribute significantly to nutrition. Pectin is widely found in plants such as citrus, apple, and cactus.

However, there is a lack of scientific evidence for the efficacy of fibre materials such as corn fibre, guar gum and gum acacia as anti-hyperlipidaemic agents. Moreover, the anti-hyperlipidaemic effect is often compromised by the high doses which are necessary with certain plant fibres; for example, psyllium is given at a dose of up to 10.2 g/day. Without sufficient water intake, these high doses of fibre often increase the risk of bowel obstruction. Safety issues also arise for plant fibre products such as glucomannan, which can cause choking due to its high swelling index, and beta-glucan, which can provoke allergic attacks in individuals with gluten allergy. Additionally, the consumption of large amounts of dietary fibre often has unwanted side-effects such as flatulence, and a diet comprising more than 60 g fibre per day may result in deficiencies of minerals such as calcium, iron, or zinc.

Various species of cactus, which are commonly widely found in Mexico, some South American countries, and other arid and semi-arid parts of the world, are widely grown as food crops. The most important of these domesticated species of cactus is *Opuntia ficus-indica*, whose fruits (tunas) and leaves (nopalitos) are consumed, and this cactus has also been proposed as an industrial source of pectin.

The pectin in *Opuntia ficus-indica* is reported to be effective in lowering serum cholesterol by a mechanism similar to that of bile acid binding, resulting in an increase in fecal bile acid excretion, which may then increase hepatic synthesis of bile acids and liver depletion of cholesterol, resulting in a higher rate of endogenous cholesterol synthesis and reduced serum cholesterol concentrations (Fernandez et al: J. Nutr. 1990 120 1283-1290; J. Nutr. 1992 122 2330-2340; J. Nutr. 1994 124 817-824). However, these experimental approaches yielded inconsistent results, which have not been independently confirmed. Hence the mechanisms underlying the effects of pectin have not yet been clearly elucidated.

Powdered preparations of various plant parts of *Opuntia ficus-indica* are commercially available. In most cases these use dried and powdered plant parts, which have not been subjected to any other processing.

European Patent No. 1377183 discloses a preparation having the property of fixing fats, derived from natural cactus cladodes of *Opuntia ficus-indica*. This preparation is in the form of a powder comprising particles at least 70% of which by weight are smaller than 100 µm, and is produced without chemical conversion or addition, thus maintaining the native fat-binding ability of the fibres. This specification emphasizes the fat-fixing or binding capability of the cactus fibre, based on a specific ratio between fat and fibre.

Other plants, such as *Camellia sinensis, Ascophyllum nodosum, Tellima grandiflora, Garcinia cambogia,* and *Salacia reticulata* have been historically used as anti-hyperlipidaemic agents, either as single active ingredients or in combination. In particular, extracts of *Salacia reticulata* are widely used in Ayurvedic medicine and in Japan for the prevention and treatment of hyperglycaemia, diabetes and other conditions. Various components of this extract have hypoglycaemic effects, inhibit the activity of a number of enzymes involved in carbohydrate metabolism, and increase insulin sensitivity. The aqueous extract from the stem and root of *Salacia reticulata* has potent alpha-glucosidase and alpha-amylase inhibitory activity.

It is reported that cyclodextrins, especially alpha-cyclodextrin, may have a beneficial effect on blood lipid levels or preventing body weight gain. However, a very high daily dosage is needed to show any significant effect.

Among the methods proposed in the art for maintaining healthy blood cholesterol levels and control of body weight is the control of fat absorption from the diet. Many options for achieving this control have been proposed, but the degree of success varies. The prior art methods have the problems of requiring a high dosage to bring about any observed effect, and adverse side-effects such as flatulence, diarrhea, abdominal cramps and bloating associated with the consumption of a high fibre diet. These factors limit the acceptability of the prior art products to consumers because of the unpleasantness of the side-effects and the relatively high cost of treatment or maintenance. Therefore there is a continued need for new compositions and methods for maintaining healthy blood cholesterol levels and control of body weight and/or obesity.

SUMMARY OF THE INVENTION

The present invention relates to a composition comprising a plant or non-plant fibre product and a cyclodextrin, and to the preparation and use of this composition.

In a first aspect, the invention provides a composition for reducing absorption of dietary fat, comprising
(a) a dietary fibre preparation of plant or non-plant origin, and
(b) at least one cyclodextrin.

The cyclodextrin is provided in a sufficient amount whereby the fat-binding ability of the fibre is increased relative to a composition without a cyclodextrin component.

In one form, the invention provides a composition comprising a blend of a dietary fibre preparation of plant or non-plant origin and at least one cyclodextrin to reduce absorption of dietary fat.

In an alternative form, the invention provides a consumable healthcare preparation for reducing absorption of dietary fat, comprising
(a) a dietary fibre preparation of plant or non-plant origin, and
(b) at least one cyclodextrin.

The cyclodextrin is provided in a sufficient amount whereby the fat-binding ability of the fibre is increased relative to a composition without a cyclodextrin component.

In another form, the invention provides a consumable healthcare preparation comprising a blend of a dietary fibre preparation of plant or non-plant origin and at least one cyclodextrin to reduce absorption of dietary fat.

The consumable healthcare preparation may for example be a dietary supplement or a meal replacement product.

It will be clearly understood that the compositions of the invention may be incorporated into any product form suitable for oral consumption, or for any other known or otherwise effective form of oral delivery. In some embodiments the dietary fibre preparation comprises insoluble fibre. In some embodiments the dietary fibre preparation comprises soluble fibre. In some embodiments the dietary fibre preparation comprises both insoluble and soluble fibre.

As defined herein, a dietary fibre of plant origin comprises any edible plant fibre which traps, absorbs or otherwise binds with fat.

As defined herein, a dietary fibre of non-plant origin comprises any edible polysaccharide derivative, including chitosan, which traps, absorbs or otherwise binds with fat.

In some embodiments the dietary fibre preparation is derived from an edible Cactaceae plant belonging to the family Opuntioideae, more particularly to the genus *Opuntia*, and even more particularly to the species *Opuntia ficus-indica*. In some embodiments the dietary fibre preparation is derived from cladodes of *Opuntia ficus-indica*.

In other embodiments, the Cactaceae species is derived from *Opuntia mbusta, Opuntia amylacea, Opuntia steptracantha, Opuntia megacantha,* and *Opuntia cochenillifera,* or a derivative thereof.

In still other embodiments the dietary fibre preparation is derived from the group of soluble fibres, including but not limited to gum acacia, guar gum, low-methoxy and high-methoxy pectin, oat and barley beta glucans, carrageenan, psyllium and derivatives thereof; and from the group of insoluble fibres, including but not limited to oat hull fibre, pea hull fibre, soy hull fibre, soy cotyledon fibre, sugar beet fibre, cellulose, corn bran, and derivatives thereof, or from a combination of one or more of these soluble and insoluble fibres.

As used herein, the term "cyclodextrin" includes unsubstituted alpha-, beta-, and gamma-cyclodextrin, and substituted alpha-, beta- and gamma-cyclodextrins such as hydroxyalkyl-, alkyl-, sulphoallylether-, glycosylated-, maltosylated-, and partially-acetylated alpha-, beta- and gamma-cyclodextrins, and their polymeric derivatives and combinations of two or more thereof.

A "Polymeric derivative" of a cyclodextrin refers to a cross-linked cyclodextrin in which the monomers are covalently linked to each other via epichlorohydrin or other suitable bifunctional chemical reagent. The average molecular mass of the water-soluble cyclodextrin polymers is preferably between 1800-5000 Dalton.

In some embodiments the cyclodextrin is gamma-cyclodextrin.

In some embodiments the composition comprises dietary fibre preparation and cyclodextrin in a weight ratio between 1:99 and 99:1.

In one embodiment the weight ratio of the dietary fibre preparation and cyclodextrin is between 95:5 and 60:40. In another embodiment the weight ratio of the dietary fibre preparation and cyclodextrin is between 85:15 and 65:35.

The product may be formulated together with other ingredients, including other active ingredients, which may be added to the composition or may be complexed to the cyclodextrin ring to form a protected inclusion complex. The latter is especially useful if the formulation comprises bitter-tasting ingredients, or volatile or degradation-sensitive materials such as flavours and some vitamins.

In a second aspect, the invention provides a composition or consumable healthcare preparation as described above suitable for treating hyperlipidaemia and/or obesity.

In a third aspect, the invention provides a composition or consumable healthcare preparation as described above and a biologically-active agent suitable for treating obesity.

In a fourth aspect, the invention provides a composition or consumable healthcare preparation as described above and a biologically-active agent suitable for treating hyperlipidaemia.

In the second, third and fourth aspects the biologically-active agent may be selected from the group consisting of absorption-altering agents, including pharmaceutically-active agents such as orlistat and cetilistat, or naturally-derived ingredients such as white kidney bean extract; appetite-altering agents, including pharmaceutically-active agents such as sibutramine, phentermine, diethylpropion, rimonabant and benzphetamine, or naturally-derived ingredients such as potato starch and glucomannan; metabolism-altering agents such as moxonidine or naturally-derived ingredients such as extracts of green tea, *Citrus aurantium*, or *Garcinia cambogia*; cholesterol-lowering agents, including pharmaceutically-active agents, such as statins (e.g. atorvastatin, simvastatin, lovastatin, pravastatin, rosuvastatin etc.), fibrates (e.g. gemfibrozil, bezafibrate, fenofibrate or ciprofibrate), vitamin B3 (niacin), bile acid sequestrants (e.g. colestipol, cholestyramine) or naturally-derived ingredients such as plant sterol compounds (e.g. sitosterol, stigmasterol, campesterol), or any combination thereof.

An oral consumable healthcare preparation used for reducing absorption of fat may occasionally cause undesirable effects; for example a preparation which reduces fat absorption may affect the absorption of fat-soluble vitamins, consuming a diet high in fibre may result in reduced calcium absorption, and so forth. A nutrient ingredient may be added to mitigate such a risk.

Therefore, the consumable healthcare preparation according to the invention may additionally comprise a nutrient ingredient. The nutrient ingredient may be selected from the group consisting of vitamins and minerals, and any combination thereof.

The vitamin may be any of a variety of vitamins or related nutrients, non-limiting examples of which include vitamin A, vitamin D, vitamin E, vitamin K, thiamine, riboflavin, pyridoxine, vitamin B12, carotenoids (e.g., beta-carotene, zeaxanthin, lutein, lycopene), niacin, folic acid, pantothenic acid, biotin, vitamin C, choline, inositol, salts and derivatives thereof, and combinations thereof. It should be noted that lipid-soluble vitamins and nutrients are likely to bind to the active agents of the composition, and therefore may be poorly absorbed.

The mineral may be any of a variety of minerals, non-limiting examples of which include calcium, phosphorus, magnesium, iron, zinc, manganese, copper, iodine, sodium, potassium, molybdenum, selenium, chromium, chloride, and combinations thereof.

In some embodiments, the composition or consumable healthcare preparation is in a suitable oral dosage form, for example tablet, caplet, softgel, powder, solution, suspension, emulsion, gel and so forth.

The composition or consumable healthcare preparation may further include one or more carriers, diluents or pharmaceutically acceptable excipients. In some embodiments the carrier, diluent, and other excipients are selected depending on the route of administration, and persons skilled in the art will be able to determine the most suitable formulation for each particular case. In one embodiment, the excipient is selected from the group consisting of anti-adherents, binders, coatings, disintegrants, fillers and diluents, flavour, colours, glidant, lubricants, preservatives, sorbents, sweeteners and combinations thereof.

Methods and pharmaceutical carriers for preparation of pharmaceutical compositions and dosage forms are well known in the art, for example as set out in textbooks such as Remington's Pharmaceutical Sciences, 20th Edition, Williams & Wilkins, Pennsylvania, USA.

In other embodiments, the consumable healthcare preparation may be formulated to modify the release of biologically-active agents. The oral dosage forms may be enteric-coated or surface-coated with retardant to control and/or delay the dissolution of the biologically-active agents. Alternatively, a dosage form which incorporates retardant excipients to provide matrix-forming sustained or modified release, or biologically-active agents which are coated or encapsulated to modify dissolution and release profiles, may be used to suit different combinations of biologically-active agents and nutrients, or for the purpose of maximizing the bioavailability and physiological effect, particularly if the dosage form comprises the composition of the invention and additional nutrients.

In a fifth aspect, the invention provides a method of reducing absorption of dietary fat, comprising the step of administering a composition or healthcare preparation according to the invention to a subject in need of such treatment.

In a sixth aspect, the invention provides a method of reducing weight gain, comprising the step of administering a composition or healthcare preparation according to the invention to a subject in need of such treatment.

In a seventh aspect, the invention provides a method of treatment of obesity, comprising the step of administering a composition or healthcare preparation according to the invention to a subject in need of such treatment.

In an eighth aspect, the invention provides a method of treatment of hyperlipidaemia, comprising the step of administering a composition or healthcare preparation according to the invention to a subject in need of such treatment.

In a ninth aspect, the invention provides the use of a composition or healthcare preparation according to the invention for:
(a) reducing absorption of dietary fat,
(b) treating obesity,
(c) reducing weight gain,
(d) maintaining a healthy blood lipid or cholesterol level, or
(e) treating hyperlipidaemia.

In a tenth aspect, the invention provides the use of a composition or healthcare preparation according to the invention in the manufacture of a medicament for:
(a) reducing absorption of dietary fat,
(b) treating obesity,
(c) reducing weight gain,
(d) maintaining a healthy blood lipid or cholesterol level, or
(e) treating hyperlipidaemia.

In an eleventh aspect, the invention provides a composition or healthcare preparation according to the invention for:
(a) reducing absorption of dietary fat,
(b) treating obesity,
(c) reducing weight gain,
(d) maintaining a healthy blood lipid or cholesterol level, or
(e) treating hyperlipidaemia.

The composition or healthcare preparation is orally administered daily to the subject. The composition or healthcare preparation is desirably administered with or after a meal, depending on the nature of the oral dosage form; for example, a capsule or powder may be administered approximately 30 minutes to one hour after a meal.

The subject is a mammal. The mammal may be a human, or may be a domestic, companion or zoo animal. While it is particularly contemplated that the compositions of the invention are suitable for use in humans, they are also applicable to veterinary treatment, including treatment of companion animals such as dogs and cats, domestic animals such as horses, cattle and sheep, or zoo animals such as non-human primates, feuds, canids, bovids, and ungulates.

Dosage will be at the discretion of the attendant physician or veterinarian, and will depend on the nature and state of the condition to be treated, the age and general state of health of the subject to be treated, and any previous treatment which may have been administered. It is contemplated that a wide range of doses may be used, due to the non-toxic nature of the composition. For example the dose may be up to 7.5 g per day.

In some embodiments the doses are in the range of 500 mg-1.5 g per meal, given 2 to 3 times a day. Thus the dose may be 500, 555, 600, 650, 700, 750, 800, 850, 900, 1000, 1050, 1100, 1150, 1200, 1250, 1300, 1350, 1400, 1450, or 1500 mg per meal.

In a twelfth aspect, the invention provides a method of preparing a blend of a composition according to the invention, comprising the steps of:

(a) mixing a dietary fibre preparation of plant or non-plant origin with at least one cyclodextrin;
(b) adding water,
(c) subjecting the thus-formed mixture to a shear force at about ambient temperature until blended to homogeneity;
(d) drying the blend to achieve a water content of 5% or below; and
(e) reducing the particle size of the dried blend.

For example, the shear force in step (d) may suitably be applied by co-kneading using twin-screw kneaders, followed by extrusion; the particle size reduction in step (f) may be achieved by means of milling and sieving with a suitably-sized mesh screen, such as EP sieve number 5 or number 10.

It will be appreciated that a simple physical mixture of a dietary fibre preparation of plant or non-plant origin, a cyclodextrin and any other ingredients may be prepared by mixing methods well known in the art.

In a thirteenth aspect, the invention provides a method of increasing the fat-binding ability of a dietary fibre preparation of plant or non-plant origin, comprising the step of subjecting the fibre to a physical interaction with a cyclodextrin.

DETAILED DESCRIPTION OF THE INVENTION

Figure 1:
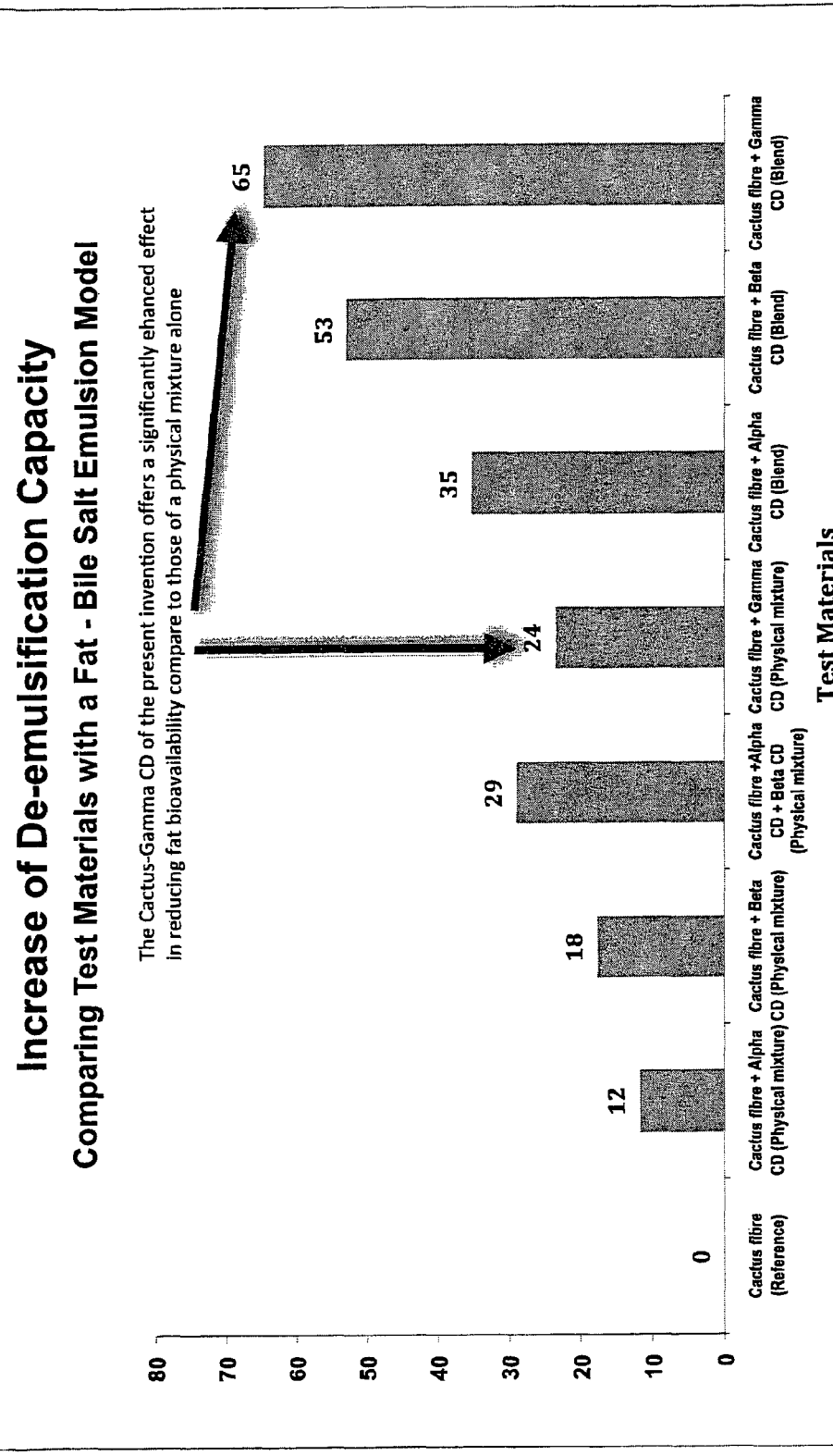
FIG. 1 is a graph illustrating the effect of various compositions of cactus fibre and cyclodextrin on bioavailability of fat in a model emulsion.
Figure 2:
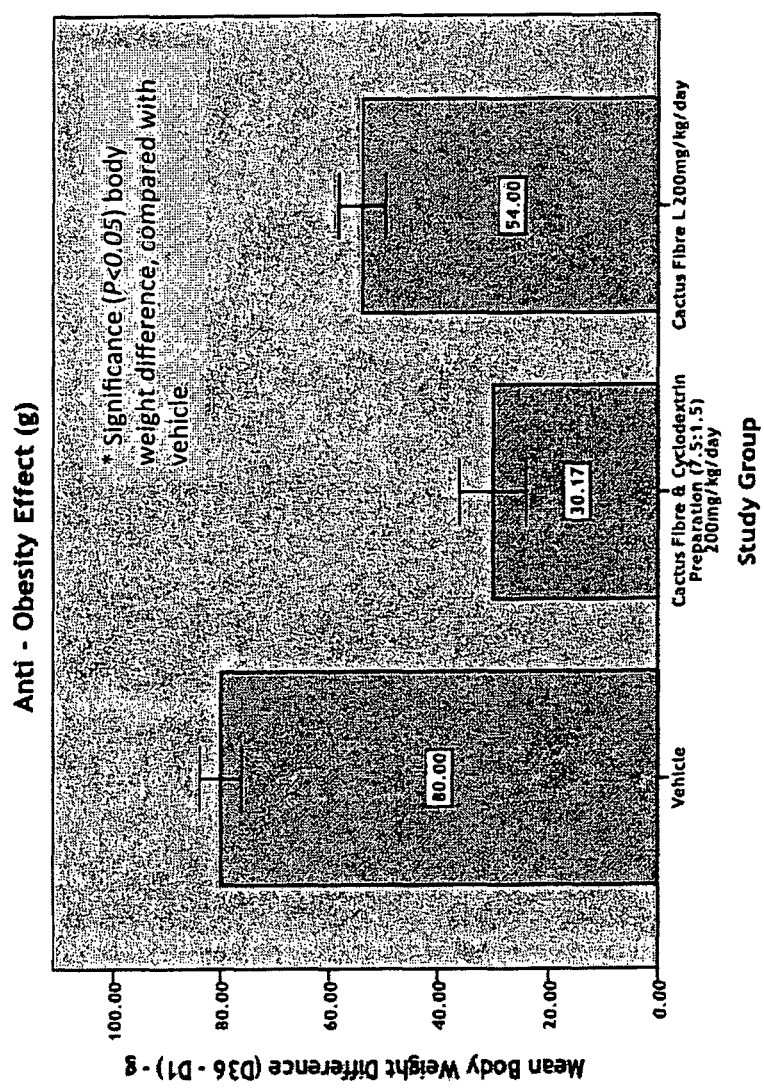
FIG. 2 is a graph illustrating the anti-obesity effect of vehicle (spring water), first treatment group (cactus fibre & gamma-cyclodextrin preparation at 7.5:1.5) and second treatment group (cactus fibre).
Figure 3:
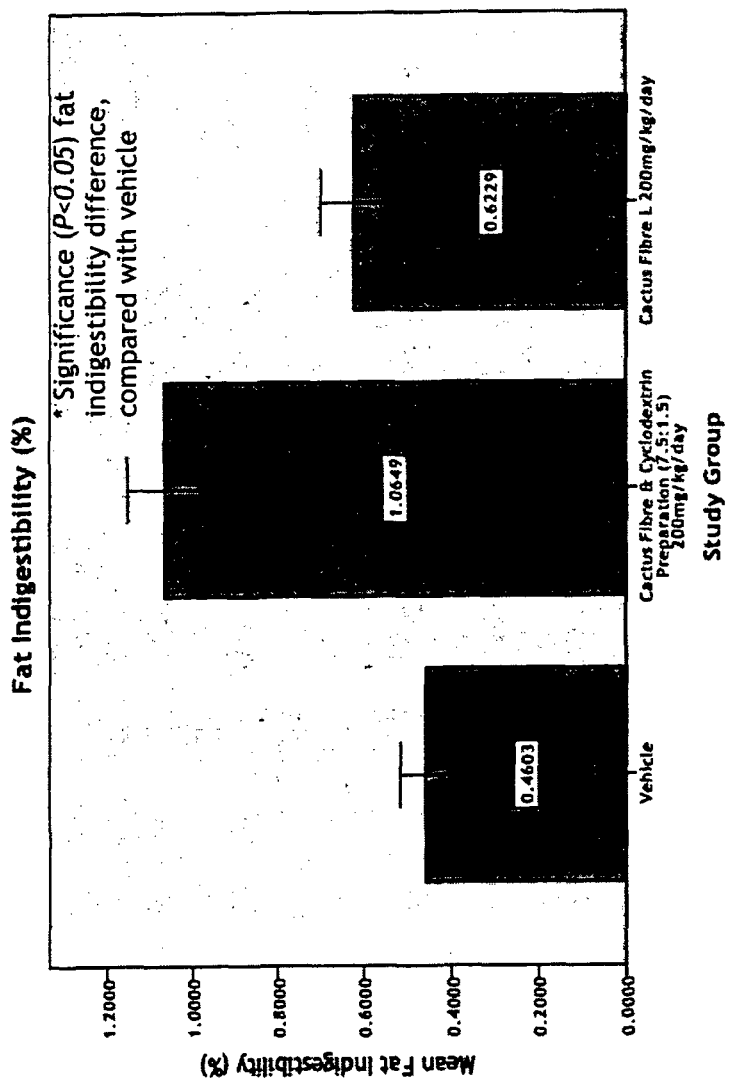
FIG. 3 is a graph illustrating the fat indigestibility of vehicle (spring water), first treatment group (cactus fibre & gamma-cyclodextrin preparation at 7.5:1.5) and second treatment group (cactus fibre).

As described herein, a "consumable healthcare preparation" is a dietary or health supplement which is adapted to be consumed by mouth, but is not in itself a food.

An "edible" plant or product means one which can be ingested by humans or animals without causing any major adverse effects. Very minor and/or transient adverse effects may be tolerated.

"Fibre" is a polysaccharide constituent which is not degraded into absorbable units within the stomach or small intestine. Soluble fibres are more soluble in water relative to insoluble fibres. Dietary fibre is further classified as being either fermentable or non-fermentable, depending on whether or not undigested fibres are digested by microbes in the large bowel.

The expression "bioavailability of fat" refers to the degree and rate at which fats are absorbed into the body from the gut.

The expression "absorption of dietary fat" refers to the process by which the products of digestion of fats present in the diet pass through the gut mucosa into the blood or lymph. Dietary fat is predominantly neutral fat or triglyceride, and also includes phospholipids, sterols such as cholesterol, and many minor lipids, including fat-soluble vitamins. The small intestine also contains lipids from sloughed epithelial cells and cholesterol delivered in bile. In order for the triglyceride to be absorbed, large aggregates of dietary triglyceride, which are virtually insoluble in an aqueous environment, must be broken down physically and held in suspension; this process is called emulsification. Triglyceride molecules must also be enzymatically digested to yield monoglyceride and fatty acids, which can efficiently diffuse or be transported into the enterocytes. These two processes are mediated by bile salts and pancreatic lipase, both of which are mixed with chyme and act in the lumen of the small intestine. Bile salts are also necessary to solubilize other lipids, including cholesterol.

"Cactus fibre" refers to Cactus fibre powder produced from a cactus belonging to the family Opuntioideae. In one form of the invention, this powder is produced from *Opuntia ficus-indica* by the method described in US patent application No. US 20040126444.

"Cyclodextrins" (CD), sometimes called cyclic dextrins, are enzyme-modified starch derivatives, cyclic malto-oligomers made up of D-glucose units. (Szejtli, J.: Cyclodextrin Technology, Kluwer Ed. Dordrecht, Holland, 1988.) The industrially-produced, commercially-available cyclodextrins are called alpha-, beta- and gamma-cyclodextrins. They consist of six, seven or eight glucose units, linked via alpha-1,4-glycosidic bonds. Alpha-cyclodextrin is cyclohexaamylose, beta-cyclodextrin is cycloheptaamylose and gamma-cyclodextrin is cyclooctaamylose. All three classes of cyclodextrins are considered by regulatory authorities as falling into the category of products which are "generally recognised as safe". As used herein, the term "cyclodextrin" also includes substituted alpha-, beta- and gamma-cyclodextrins, such as hydroxyalkyl-, alkyl-, sulphoallylether-, glycosylated-, maltosylated-, and partially acetylated-alpha-, beta- and gamma-cyclodextrins, their polymeric derivatives, and any combinations thereof. The cyclodextrin as used herein could further extend to the use of dextrin group which also includes maltodextrin and its derivatives thereof.

A "Polymeric derivative" of a cyclodextrin refers to a cross-linked cyclodextrin in which the monomers are covalently linked to each other via epichlorohydrin or other suitable bifunctional chemical reagent. The average molecular mass of the water-soluble cyclodextrin polymers is preferably between 1800-5000 Dalton.

A "Blend" as referred to in the Examples herein is a solid preparation formed by mixing dietary fibre and a cyclodextrin under conditions whereby the cyclodextrin is enabled to interact with the fibrous matrix of the dietary fibre, for example by subjecting the dietary fibre and cyclodextrin to shear force.

"De-emulsifying ability", "De-emulsifying effect" or "De-emulsifying efficiency" means the removal of digestible micrometer-scale lipid droplets from a model chyme (emulsion) by inducing them to coalesce and thus transforming them into indigestible millimeter-scale droplets. The de-emulsifying ability of a composition or agent serves as a predictor of its ability to inhibit emulsification of lipids in the gut, and hence to inhibit lipid absorption. The de-emulsifying ability is also correlated with the fat-binding ability or fat elimination ability of the composition.

The term "fat" as used herein, unless otherwise specified, means oils, lipids, greasy materials, or combinations thereof.

"Hyperlipidaemia" is an elevation of lipids in the bloodstream. These lipids include cholesterol, cholesterol esters, phospholipids and triglycerides.

A "bile salt" is a natural surfactant which is essential for efficient digestion and absorption of fats for metabolism. Bile salts are bile acids conjugated to either glycine or taurine. In humans, the most important bile acids are cholic acid, deoxycholic acid, and chenodeoxycholic acid. Prior to secretion by the liver, they are conjugated with glycine or taurine. Bile salts act to some extent as detergents, helping to emulsify fats into a finely dispersed microemulsion. By increasing the interfacial surface area of fats in chyme (the semi-fluid mass of partly-digested food expelled by the stomach into the duodenum), bile salts assist the enzymatic action of lipases, and thus aids fatty acid absorption from the small intestine. If bile salts are absent from the duodenum, or if they are bound so that their action is blocked, not all fats are able to be digested, and the non-absorbed fat is excreted in the feces.

In some embodiments the composition comprises a dietary fibre and a cyclodextrin in a weight ratio between 1:99 and 99:1. Thus the ratio may be 1:99, 2:98, 3:97, 4:96, 5:95, 6:94, 7:93, 8:92, 9:91, 10:90, 11:89, 12:88, 13:87, 14:86, 15:85, 16:84 17:83, 18:82, 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:56, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, or 99:1.

In one embodiment the weight ratio of the dietary fibre and a cyclodextrin is between 95:5 and 60:40. In another embodiment the weight ratio of the dietary fibre and a cyclodextrin is between 85:15 and 65:35.

An in vitro model which simulates the in vivo bile-fat chyme (emulsion) was developed to evaluate the efficacy of the study materials.

The emulsion prepared with Na-deoxycholate was found to be the most suitable model chyme, since it distinguished changes which are of significance in the process of fat digestion, showing a clearer and consistent result. However, emulsions prepared from soy lecithin may also be used.

The model fat-Na-deoxycholate emulsions showed suitable stability for relatively rapid comparison laboratory tests. The changes in stability were recorded when these emulsions were exposed to the effect of cactus powder, apple fibre, oat fibre, shark cartilage, chondroitin sulphate, chitosan, cyclodextrins, or combinations of each of these fibres with cyclodextrin. Phase separation studies were then developed to enable the visualization and quantification of de-emulsification process over time.

An exponential increased de-emulsification effect was demonstrated for certain fibre/cyclodextrin combinations in the experimental fat-bile salt emulsion model using a blended composition according to the invention. The degree of de-emulsification of the model fat-bile salt emulsion caused by the composition serves as a predictor of the ability of compositions of the invention to inhibit emulsification of lipids in vivo by bile salts, and consequently to inhibit dietary fat absorption.

Without wishing to be limited by any proposed mechanism for the observed increased effects, we believe that certain dietary fibres undergo a physical interaction when blended with a cyclodextrin, which substantially increases their fat-binding or fat elimination ability, and that the structural alterations taking place during the physical interaction together with the properties of the native ingredients result in an increased effect in reducing dietary fat absorption. Thus, in addition to the use of a much lower dose of a cyclodextrin than has been proposed in the prior art, the physical interaction between certain dietary fibres and cyclodextrin has not been previously disclosed or suggested.

We have found that the de-emulsification of fat by dietary fibres of plant and non-plant origin, and in particular cactus fibre, apple fibre and chitosan, in an in vitro experimental fat-bile salt emulsion model can be improved by prior processing with a cyclodextrin. We have also demonstrated in this model that a low dosage of cyclodextrin in a blend with certain plant fibres, including cactus fibre or apple fibre, exerts higher efficacy than that of prior art compositions which use a much higher dose of cyclodextrin, thereby lowering the cost of prevention or treatment.

In the in vitro studies with the model emulsion, the Cactus fibre alone was found to be an effective de-emulsifying agent in that resulted in agglomeration of micro-scale droplets of the emulsion, eventually causing phase separation of, the fat and water in the emulsion. It was also demonstrated that cyclodextrin alone does not produce a de-emulsification effect in the model emulsion. This phenomenon is likely to be attributable to the affinity of surfactants to the cactus fibres. The extent of de-emulsification elicited by the test materials was used as a predictor of the ability of these materials to reduce fat bioavailability in vivo. While we believe that the specific class or identity of the cyclodextrin in the aforementioned experiments is not important, gamma-cyclodextrin was found to be the most efficient.

In a series of further studies, it was demonstrated that while both the simple physical mixture and the prior processed blend of the Cactus fibre with cyclodextrins resulted in increased de-emulsification ability compared to effect of the cactus fibre alone, an exponential increase in de-emulsification effect was observed only with the emulsion treated with a Cactus fibre-cyclodextrin blend. Similar exponential increase in de-emulsification was demonstrated when apple fibre was blended with cyclodextrin. Of the cyclodextrins tested, the most significant synergism was observed with the prior-processed blend of gamma cyclodextrin and Cactus fibre, as illustrated in FIG. 1.

The results of the in vitro tests suggest that a composition comprising Cactus fibre and gamma-cyclodextrin in a solid blend formula is particularly suitable for effective weight management. The efficacy of the composition may readily be tested in vivo, using methods well known in the art.

In a particular embodiment of the present invention, the composition of Cactus fibre and a cyclodextrin may further comprise a biologically-active agent suitable for treating obesity and hyperlipidaemia. The biologically-active agent may be selected from the group consisting of absorption-altering agents, including pharmaceutically-active agents such as orlistat and cetilistat, or naturally-derived ingredients such as white kidney bean extract; appetite-altering agents, including pharmaceutically-active agents such as sibutramine, phentermine, diethylpropion, rimonabant and benzphetamine, or naturally-derived ingredients such as potato starch and glucomannan; metabolism-altering agents such as moxonidine or naturally-derived ingredients such as extracts of green tea, *Citrus aurantium*, or *Garcinia cambogia*; cholesterol-lowering agents, including pharmaceutically-active agents, such as statins (e.g. atorvastatin, simvastatin, lovastatin, pravastatin, rosuvastatin etc.), fibrates (e.g. gemfibrozil, bezafibrate, fenofibrate or ciprofibrate), vitamin B3 (niacin), bile acid sequestrants (e.g. colestipol, cholestyramine) or naturally-derived ingredients such as plant sterol compounds (e.g. sitosterol, stigmasterol, campesterol), or any combination thereof.

In another particular embodiment of the present invention, the composition of Cactus fibre and cyclodextrins may further comprise a nutrient ingredient selected from the group consisting of vitamins and minerals, and any combination thereof. The vitamin may be any of a variety of vitamins or related nutrients, non-limiting examples of which include vitamin A, vitamin D, vitamin E, vitamin K, thiamine, riboflavin, pyridoxine, vitamin B12, carotenoids (e.g., beta-carotene, zeaxanthin, lutein, lycopene), niacin, folic acid, pantothenic acid, biotin, vitamin C, choline, inositol, salts and derivatives thereof, and combinations thereof. The mineral may be any of a variety of minerals, non-limiting examples of which include calcium, phosphorus, magnesium, iron, zinc, manganese, copper, iodine, sodium, potassium, molybdenum, selenium, chromium, chloride, and combinations thereof.

The invention will now be described in detail by way of reference only to the following non-limiting examples and drawings. All compounds and materials used in the examples are commercially available.

EXAMPLES

Cactus Powder

The cactus powder used in the experiments described herein is produced from *Opuntia ficus-indica* by the method described in US patent application (publication number US20040126444). The fibre complex contains two kinds of fibre, in approximately equal proportions: insoluble fibre and soluble fibre. The insoluble fibre is a polymer, insoluble in water at neutral pH and ambient temperature. The soluble fibre is a soluble polysaccharide dietary fibre containing pectin, gum and mucilage, which form a fluid gel in the stomach. The increase of pH from stomach to small intestine does not affect the gel's stability.

The pectin component of *Opuntia ficus-indica* fibre is both low-methoxy (ie degree of methoxylation <50%) and high-methoxy (ie degree of methoxylation >50%); the relative proportions of low-methoxy and high-methoxy depend on the part of the cactus (Goycoolea F. M. and A. Cardenas: "Pectins from *Opuntia* spp: a short review" J. PACD 2003 17-19). The fibre complex from *Opuntia ficus-indica* contains dietary fibre (about 45%), soluble sugars, proteins, lipids, vitamins minerals (mainly calcium and phosphorus) and amino acids. The cactus powder may optionally comprise granulated gum acacia excipient in the range of 5 to 35% as a granulation aid.

Apple fibre, oat fibre, cartilage, chondroitin and chitosan tested herein for de-emulsifying effects were obtained from the following sources with the described specifications:

| Test Material | Source | Specification |
|---|---|---|
| Apple Fibre | Plant | >50% dietary fibre |
| Oat Fibre | Plant | >90% dietary fibre |
| Cartilage | Animal (Shark) | ≥40% Protein |
| Chondroitin | Animal (Shark) | >90% Chondroitin sulphate |
| Chitosan | Animal (Crustaceans) | >70% Deacetylation degree |

Surfactant:
  Sodium deoxycholate: product of Sigma-Aldrich (>97%):
  Sodium dodecyl sulphate (SDS): product of Merck (>99.0%);
  Soy bean lecithin: commercial food supplement (96%) (BiYo-Product Ltd., Hungary)
Cyclodextrins:
  alpha-cyclodextrin (CYL-2322);
  beta-cyclodextrin (CYL-2518/2);
  gamma-cyclodextrin (CYL-2323):
  each a product of CycloLab Ltd., Hungary
Other Reagents:
  Sunflower oil: commercial food grade product: "Vénusz" brand (product of Bunge Ca., Hungary)
  Sudan red, an oil-soluble dye (product of Reanal, Hungary)
All other reagents used were of analytical grade commercial products, and distilled water was used in all experiments.

Example 1

Model Chyme

Fat-Na Deoxycholate Emulsion

The model emulsion was composed of,
  48 g sunflower oil (saturated with Sudan red)
  350 g distilled water
  0.58 g sodium deoxycholate
and was prepared by homogenization in an Ultra-turrax homogenizer for 5 min at 9000 RPM.

Example 2(a)

Preparation of Gamma-Cyclodextrin and Cactus Fibre Blend 600 g dried plant fibre composition originating from species *Opuntia ficus indica* was triturated with 300 g of previously amorphized gamma-Cyclodextrin powder. After addition of 200 ml water, the mixture was treated by means of shear force mechanical activation by co-kneading by a twin-screw kneader, at ambient temperature for 30 minutes until a homogenous blend was obtained, followed by extrudation. The water content of the blend was removed in vacuo at 40° C. to below 5.0 w %. The dried blend was granulated and sieved to break any lumps into powder; the particle size is not critical.

(b) In a similar manner were prepared blends of either alpha- or beta-Cyclodextrin with cactus fibre.

(c) Similarly prepared was a blend of gamma-Cyclodextrin and Cactus fibre in a ratio of 1.5:7.5 using 150 g gamma-Cyclodextrin and 750 g cactus fibre.

(d) Similarly prepared were blends of gamma-Cyclodextrin and other plant fibres and non-plant fibres, including apple fibre, oat fibre, shark cartilage, chondroitin sulphate and chitosan

Example 3(a)

Preparation of Physical Mixture of Gamma-Cyclodextrin and Cactus Fibre 600 g dried plant fibre composition originating from the species *Opuntia ficus-indica* was triturated with 300 g of previously amorphized gamma-cyclodextrin powder. The physical powder mixture was homogenized by dry blending and used without further treatment.

(b) In a similar manner were prepared physical mixtures of either alpha- or beta-Cyclodextrin with cactus fibre.

(c) Similarly prepared was a physical mixture of gamma-Cyclodextrin and Cactus fibre in a ratio of 1.5:7.5 using 150 g gamma-Cyclodextrin and 750 g cactus fibre.

(d) Similarly prepared were physical mixtures of gamma-Cyclodextrin and other plant fibres and non-plant fibres, including apple fibre, oat fibre, shark cartilage, chondroitin sulphate and chitosan

Example 4

In Vitro Efficacy of Study Materials with Model Emulsion

The test materials prepared according to Examples 2(a), 2(b), 2(d), 3(a) 3(b) and 3(d) were each added to 50 g of emulsion prepared as in Example 1, according to the schedule set out in Tables 1 and 2. The de-emulsifying effect of a test material is a measure of its ability to reduce the bioavailability of dietary fat.

TABLE 1

Test materials for evaluation of the de-emulsifying effects of Cactus fibre/cyclodextrin in the model emulsion system

| Test Sample | Cactus fibre | Alpha-CD | Beta-CD | Gamma-CD |
|---|---|---|---|---|
| Emulsion + Cactus fibre | 0.6 g | | | |
| Emulsion + Alpha-CD | | 0.3 g | | |
| Emulsion + Beta-CD | | | 0.3 g | |
| Emulsion + Alpha-CD + Beta-CD (Physical mixture) | | 0.15 g | 0.15 g | |
| Emulsion + Cactus fibre + Alpha-CD (Physical mixture) | 0.6 g | 0.3 g | | |
| Emulsion + Cactus fibre + Beta-CD (Physical mixture) | 0.6 g | | 0.3 g | |
| Emulsion + Cactus fibre + Alpha-CD + Beta-CD (Physical mixture) | 0.6 g | 0.15 g | 0.15 g | |
| Emulsion + Cactus fibre + Gamma-CD (Physical mixture) | 0.6 g | | | 0.3 g |
| Emulsion + Cactus fibre + Alpha-CD (Blend) | 0.6 g | 0.3 g | | |
| Emulsion + Cactus fibre + Beta-CD (Blend) | 0.6 g | | 0.3 g | |
| Emulsion + Cactus fibre + Gamma-CD (Blend) | 0.6 g | | | 0.3 g |

Phase Separation Study—Volumetric Test 50 g of stock emulsion was portioned on to the previously-weighed solid additives while the stock emulsion was continuously stirred gently. 50 ml of the homogenized samples were filled into a graduated cylinder so that the rate and the extent of phase separation could be observed were recorded, and the volume of the separated (upper) oil-rich emulsion phase and the quantity of pure oil layers which eventually appeared were a measure of the de-emulsifying efficiency of the additives.

During phase separation, microdroplets of oil in the emulsion coalesced into bigger oil droplets, forming a layer of oil-rich emulsion, which floated on the upper portion of the emulsion. This was indicated by the more intense Sudan red colour of the oil. A more compact oil-rich phase indicated a stronger de-emulsification capability of the test materials. After 1 hour of standing, the test samples were examined and the volume of the oil-rich phase measured. The results are shown in Table 3.

TABLE 2

Test materials for evaluation of the de-emulsifying effects of various plant/gamma-CD and non-plant/gamma CD in the model emulsion system

| Test Sample | Cactus Fibre | Gamma CD |
|---|---|---|
| Emulsion + Cactus fibre | 0.6 g | 0 g |
| Emulsion + Cactus fibre + Gamma CD (Physical mixture) | 0.5 g | 0.1 g |
| Emulsion + Cactus fibre + Gamma CD (Blend) | 0.5 g | 0.1 g |
| Emulsion + Apple fibre | 0.6 g | 0 g |
| Emulsion + Apple fibre + Gamma CD (Physical mixture) | 0.5 g | 0.1 g |
| Emulsion + Apple fibre + Gamma CD (Blend) | 0.5 g | 0.1 g |
| Emulsion + Oat fibre | 0.6 g | 0 g |
| Emulsion + Oat fibre + Gamma CD (Physical mixture) | 0.5 g | 0.1 g |
| Emulsion + Oat fibre + Gamma CD (Blend) | 0.5 g | 0.1 g |
| Emulsion + Cartilage | 0.6 g | 0 g |
| Emulsion + Cartilage + Gamma CD (Physical mixture) | 0.5 g | 0.1 g |
| Emulsion + Cartilage + Gamma CD (Blend) | 0.5 g | 0.1 g |
| Emulsion + Chondroitin | 0.6 g | 0 g |
| Emulsion + Chondroitin + Gamma CD (Physical mixture) | 0.5 g | 0.1 g |
| Emulsion + Chondroitin + Gamma CD (Blend) | 0.5 g | 0.1 g |
| Emulsion + Chitosan | 0.6 g | 0 g |
| Emulsion + Chitosan + Gamma CD (Physical mixture) | 0.5 g | 0.1 g |
| Emulsion + Chitosan + Gamma CD (Blend) | 0.5 g | 0.1 g |

Phase Separation Study—Volumetric Test 50 g of stock emulsion was portioned on to the previously-weighed solid additives and stirred continuously to form a homogenized sample. The homogenized samples were filled into a graduated cylinder so that the rate and the extent of phase separation could be observed and recorded.

During phase separation, microdroplets of oil in the emulsion coalesced into bigger oil droplets, forming a layer of oil-rich emulsion, which floated on the upper portion of the emulsion. This was indicated by the more intense Sudan red colour of the oil. A more compact oil-rich phase indicated a stronger de-emulsification capability of the test materials. After 24 hour of standing, the test samples were examined and the volume of a more compact oil-rich phase were measured. The results are shown in Table 4.

TABLE 3

Results of de-emulsification test

| Test Samples | Volume of Oil-rich Phase ($V_x$) | % Increase in De-emulsification ($D_x$) vs Reference* |
|---|---|---|
| Emulsion + Cactus fibre | 17 ml | Reference |
| Emulsion + Alpha-CD | 0 ml | No de-emulsification |

TABLE 3-continued

Results of de-emulsification test

| Test Samples | Volume of Oil-rich Phase ($V_x$) | % Increase in De-emulsification ($D_x$) vs Reference* |
|---|---|---|
| Emulsion + Beta-CD | 0 ml | No de-emulsification |
| Emulsion + Alpha-CD + Beta-CD (Physical mixture) | 0 ml | No de-emulsification |
| Emulsion + Cactus fibre + Alpha-CD (Physical mixture) | 15 ml | 12 |
| Emulsion + Cactus fibre + Beta-CD (Physical mixture) | 14 ml | 18 |
| Emulsion + Cactus fibre + Alpha-CD + Beta-CD (Physical mixture) | 12 ml | 29 |
| Emulsion + Cactus fibre + Gamma-CD (Physical mixture) | 13 ml | 24 |
| Emulsion + Cactus fibre + Alpha-CD (Blend) | 11 ml | 35 |
| Emulsion + Cactus fibre + Beta-CD (Blend) | 8 ml | 53 |
| Emulsion + Cactus fibre + Gamma-CD (Blend) | 6 ml | 65 |

*calculated according to the formula $D_x = (V_x - V_1) \div V_1 \times 100$ where x = test sample; $V_1$ = volume of oil rich phase for the Reference (test sample 1; Emulsion + Cactus fibre).

The results of this phase separation study are illustrated in FIG. 1 (Cactus fibre), and show that the method of pre-treatment (physical mixing vs. "Blending") has a very significant effect on reduction of fat bioavailability, with the Blends having a much greater effect when Cactus fibre is used. The differences in cavity sizes of the cyclodextrins may also play a role in fat removal, since there was a difference in effect between alpha-, beta- and gamma-cyclodextrin.

Therefore, it has been demonstrated that gamma-cyclodextrin in a cactus-fibre "blended" composition is superior to the other cyclodextrins as an inhibitor of fat absorption.

It will be appreciated that the same method can be used to test Blends and mixtures in which the cyclodextrin is replaced by maltodextrin or other suitable starch derivatives, and the Cactus fibre is replaced by dietary fibre selected from the group consisting of soluble dietary fibres, such as gum acacia, guar gum, citrus pectin, low- and high-methoxy pectin, oat and barley beta-glucans, carrageenan, psyllium and combinations thereof, and insoluble dietary fibres, such as oat hull fibre, pea hull fibre, soy hull fibre, soy cotyledon fibre, sugar-beet fibre, cellulose, corn bran, and combinations thereof.

TABLE 4

Results of de-emulsification test

| Test samples | Volume of Oil-rich Phase ($V_x$) | % De-emulsification, Dx* |
|---|---|---|
| Emulsion + Cactus fibre | 0 ml | 0 |
| Emulsion + Cactus fibre + Gamma CD (Physical mixture) | 0 ml | 0 |
| Emulsion + Cactus fibre + Gamma CD (Blend) | 5 ml | 50 |
| Emulsion + Apple fibre | 0 ml | 0 |
| Emulsion + Apple fibre + Gamma CD (Physical mixture) | 0 ml | 0 |
| Emulsion + Apple fibre + Gamma CD (Blend) | 1 ml | 10 |
| Emulsion + Oat fibre | 1 ml | 10 |
| Emulsion + Oat fibre + Gamma CD (Physical mixture) | 1 ml | 10 |
| Emulsion + Oat fibre + Gamma CD (Blend) | 1.5 ml | 15 |
| Emulsion + Cartilage | 0 ml | 0 |
| Emulsion + Cartilage + Gamma CD (Physical mixture) | 0 ml | 0 |
| Emulsion + Cartilage + Gamma CD (Blend) | 0 ml | 0 |
| Emulsion + Chondroitin | 2 ml | 20 |
| Emulsion + Chondroitin + Gamma CD (Physical mixture) | 2.5 ml | 25 |
| Emulsion + Chondroitin + Gamma CD (Blend) | 1 ml | 10 |
| Emulsion + Chitosan | 2.5 ml | 25 |
| Emulsion + Chitosan + Gamma CD (Physical mixture) | 7.5 ml | 75 |
| Emulsion + Chitosan + Gamma CD (Blend) | 3.5 ml | 35 |

Figure 4:
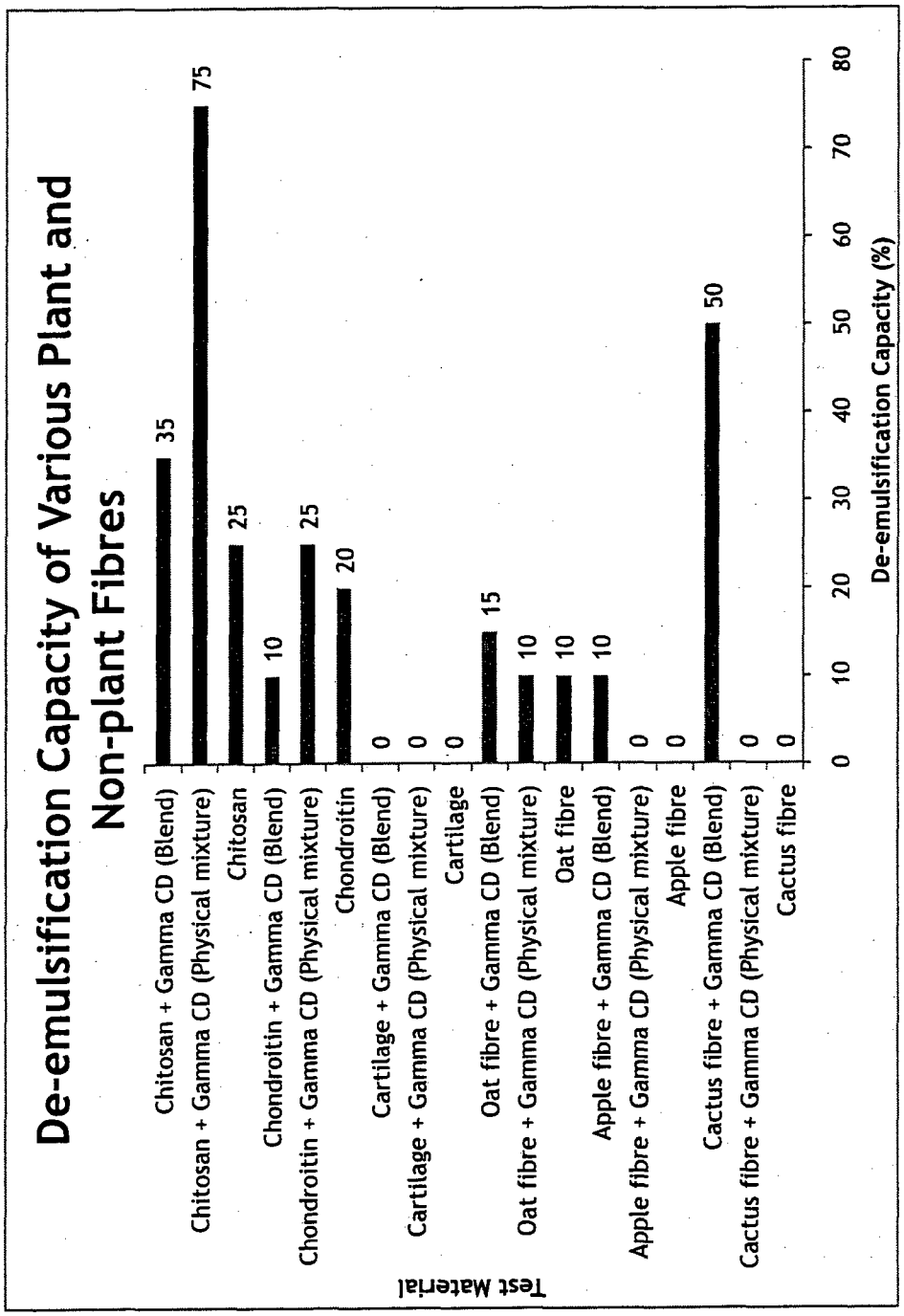
FIG. 4 is a bar chart illustrating the de-emulsification capacity of various plant and non-plant fibres.

*calculated according to the formula $Dx = (Vx/R) \times 100$ wherein R is 10 ml of compact oil in the emulsion/Negative Control The results of this phase separation study are illustrated in FIG. 4 and show (1) that certain fibres such as cartilage have no de-emulsification capacity with or without gamma-cyclodextrin and (2) that the method of pre-treatment (physical mixing vs. "Blending") can have a very significant effect on reduction of fat bioavailability, with the Blends having a much greater effect when Cactus fibre is used whereas physical mixtures have a greater effect when chitosan is used.

Example 5

Gas Chromatographic Study of Fat-Binding Efficiency

It was observed that the model emulsions containing cactus powder/cyclodextrin Blends had a fibrous sediment which sank to the bottom of the graduated cylinders. This was not observed when cyclodextrins were added to the cactus powder as a physical mixture. This phenomenon suggests that during the pre-treatment of the cactus powder by cyclodextrins ("Blending"), the cactus fibres undergo significant physical changes. Aggregated hydrophobic fibre moieties may become unfolded or swollen due to this processing, making additional regions available for triggering de-emulsification. Cyclodextrin may be extracted from the fibrous matrix by water when it comes into contact with the emulsion. Meanwhile the fibres may aggregate again, forming a separate hydrogel phase. It was very noticeable that the volume of the sediment was greatest when the Blend prepared with gamma-cyclodextrin, which showed the most efficient de-emulsifying effect, was added to the model emulsions.

We have developed a gas chromatographic method in order to determine the amount of oil bound to the cactus fibres. Aliquots were taken from the sedimented fibrous layers of a model emulsion containing soybean lecithin as emulsifier. Blends and physical mixtures of cactus fibre and cyclodextrin, prepared as in Examples 2(a), 2(b), 3(a) and 3(b) were each added to a stock emulsion of the following composition, prepared in the same way as described in Example 1:

48 g sunflower oil (saturated with Sudan red)
350 g distilled water
0.73 g soybean lecithin The sample preparation method was adapted from European Pharmacopoeia 2.4.22. 0.6-3.0 g samples comprising dissolved, bound or emulsified triglycerides (oil) were weighed exactly into test tubes. 2.00 ml hexane was added to the samples, and the mixture was vigorously shaken to extract the triglycerides into the organic phase for 30 seconds. When complete phase separation was attained, 1.00 ml of the upper (organic) phase was pipetted into test tubes. Hexane was removed by evaporation in a nitrogen stream. The remaining oil was transesterified by adding 1.0 ml methanol and 25 μl solution of potassium hydroxide in methanol (c=60 g/l). The mixtures were gently boiled for 10 min under a nitrogen atmosphere. The reaction mixture was cooled and the transesterified fatty acids were extracted by 0.80 ml hexane. The solution obtained analysed by gas chromatography, using a Shimadzu GC-17A gas chromatograph with a Supelcowax 10 column (30 m×0.32 mm×1.0 μm) Shimadzu AOC-5000 auto injector and a flame ionization detector, under standard conditions (Temperature program: injector temperature: 260° C., detector temperature: 260° C.; 170° C. initially, increased to 230° C. at 3° C./min and held for 15 min, increased to 260° C. at 15° C./min and held for 33 min) with split ratio 11:1. Shimadzu Class-VP 7.4 Version software was used.

As a reference sample, sunflower oil saturated with Sudan red dye was also transesterified and analysed. The numerical data showing the distribution of oil in the different separated phases are summarized in Table 5.

TABLE 5

Oil distribution amongst the separated phases in 50 ml of lecithin-containing model emulsions after a 24 hour storage period

| Sample | $V_{oil}$ in oil phase (ml) | $V_{oil}$ in emulsion phase (ml) | $V_{oil}$ in aqueous phase (ml) | $V_{oil}$ in fibrous phase (ml) |
|---|---|---|---|---|
| Cactus powder | 0.5 | 5.7 | Not detected | Not separated |
| Cactus powder + alpha-CD (physical mixture) | 2.0 | 4.2 | <0.001 | Not separated |
| Cactus powder + beta-CD (physical mixture) | 1.5 | 4.7 | 0.009 | Not separated |
| Cactus powder + gamma-CD (physical mixture) | 1.5 | 4.7 | Not detected | Not separated |
| Cactus powder + alpha-CD (Blend) | 5.9 | 0.31 | Not detected | 0.018 |
| Cactus powder + beta-CD (Blend) | 5.6 | 0.61 | Not detected | 0.034 |
| Cactus powder + gamma-CD (Blend) | 5.2 | 1.0 | 0.008 | 0.052 |

Oil was removed virtually completely from the aqueous phases (theoretically oil could be present in the form of micelles or phospholipid bilayers in the aqueous medium). The quantity of oil bound by the separated fibres was negligible. The highest amount was detected in the sample comprising cactus powder/gamma-cyclodextrin Blend; nevertheless this amount is only about 1% of the total initial amount of fat.

The Blends clearly showed higher de-emulsifying ability than physical mixtures. In this example cactus powder/alpha-cyclodextrin Blend removed the highest amount of fat from the emulsion state, but we have found that under these conditions the gamma-cyclodextrin-based Blend provided the highest rate of de-emulsification.

This gas chromatographic method also enabled the detection of eventual changes in the layer-by-layer distribution profile in terms of the acyl chain length of fatty acids. Preferential enrichment was not observed, ie. Oil was present in all layers in identical chemical compositions, regardless of the presence of very different quantities. Thus our results provide further support for the suggestion that the mechanism of the fat removal brought about by the cactus fibres is not likely to result from mere sorption of triglycerides into the formed fibrous phase.

Example 6

In vivo Study of Efficacy in Animals

An in vivo study was performed on female Sprague-Dawley rats, with a study duration of 5 weeks. Groups of rats (6 rats per group) were housed individually in the polycarbonate cages, and were fed with the high fat diet (Harlan, TD 06414) throughout the study duration. The control group was treated orally with vehicle (spring water), while the first treatment group was treated orally with a daily dose of 200 mg/kg/day of the test composition prepared according to Example 2(c). Meanwhile, the second treatment group was treated orally with a daily dose of 200 mg/kg/day of fibre preparation (Cactus Fibre) only. Parameters such as body weight, absolute food intake, feces consistency and animal behaviour (morbidity and mortality) were evaluated daily. Fecal fat was evaluated once on day 15.

The body weight of individual rats was measured daily, using a calibrated electronic weighing scale. The anti-obesity effect was evaluated based on the body weight different between the last treatment day (day 36) and baseline (day 1). The numerical data showing the anti-obesity effect is summarized in Table 6.

The absolute food intake was assessed with reference to food intake and spillage.

Feces consistency, morbidity and mortality were monitored by daily observation.

Feces sampling was performed on day 15 by placing the rats in the metabolic cages for 24 hours. Fecal analysis was then performed to determine the fecal fat content. The fat indigestibility (%) was determined by the ratio of total fecal fat excreted (mg) and total dietary fat intake (mg). The numerical data showing the fat indigestibility (%) is summarized in Table 7.

TABLE 6

Anti-obesity effect of first treatment group (cactus fibre & gamma-cyclodextrin preparation at 7.5:1.5) and second treatment group (cactus fibre)

| Anti-Obesity Effect (g) | Cactus Fibre & gamma-Cyclodextrin preparation (7.5:1.5) 200 mg/kg/day | Cactus Fibre 200 mg/kg/day |
|---|---|---|
| Mean Body Weight difference between treatment group and vehicle | −49.83* | −26.00 |
| Standard Deviation | 14.59 | 10.51 |

*Significant difference (P < 0.05) compared with Cactus Fibre alone

TABLE 7

Fat indigestibility of first treatment group (cactus fibre & gamma-cyclodextrin preparation at 7.5:1.5) and second treatment group (cactus fibre)

| | Cactus Fibre & gamma-Cyclodextrin preparation (7.5:1.5) 200 mg/kg/day | Cactus Fibre 200 mg/kg/day |
|---|---|---|
| Fat Indigestibility (%) | | |
| Mean Fat Indigestibility difference between treatment group and vehicle | 0.60* | 0.16 |
| Standard Deviation | 0.21 | 0.19 |

*Significant difference (P < 0.05) compared with Cactus Fibre alone

Mean body weight (MBW) difference between treatment group & vehicle (g)=[MBW of treatment group on day 36–MBW of treatment group on day 1]–[MBW of vehicle on day 36–MBW of vehicle on day 1].

Fat Indigestibility(%)=[Total fecal fat excreted/Total dietary fat intake]×100%.

Fat Indigestibility difference between treatment group & vehicle(%)=Fat indigestibility of treatment group–Fat indigestibility of vehicle.

Example 7

Tablet Formulation I

TABLE 8

Composition of tablet formulation comprising cactus powder and cyclodextrin

| Ingredient | Quantity per tablet |
|---|---|
| 1. Cactaceae-based composition comprising cactus fibre/cyclodextrin Blend | 500.0 mg |
| 2. Microcrystalline cellulose | 142.0 mg |
| 3. Calcium hydrogen phosphate dihydrate | 20.0 mg |
| 4. Silica (silicon dioxide) | 6.5 mg |
| 5. Povidone (Kollidon CL) | 24.0 mg |
| 6. Magnesium stearate | 7.5 mg |

Ingredients are dispensed according to the above formulation for a batch size of 2000 tablets. Ingredients 1 to 5 are sieved through a sieve of mesh size #20 (850 microns), and blended homogeneously in a laboratory-scale drum blender. Ingredient 6 through a sieve of mesh size #30 (600 microns) into the powder mixture, and further blended for 1 minute. The mixture is compressed into oblong tablets of 700 mg each using a rotary tablet press. The tablet hardness is approximately 200 kN, and disintegration time <60 minutes

Example 8

Tablet Formulation II

TABLE 9

Composition of tablet formulation comprising cactus powder and cyclodextrin

| | Quantity per tablet |
|---|---|
| Ingredients (A) | |
| 1. Cactaceae-based composition comprising cactus fibre/cyclodextrin Blend | 500 mg |
| 2. Sodium selenite | 2 mg |
| 3. Chromium chloride hexahydrate | 24 mg |
| 4. Microcrystalline cellulose | 122 mg |
| 5. Calcium hydrogen phosphate | 20 mg |
| 6. Sodium starch glycolate | 25 mg |
| 7. Magnesium stearate | 7 mg |
| Ingredients (B) | |
| 1. Calcium carbonate | 250 mg |
| 2. Zinc gluconate | 8 mg |
| 3. Vitamin A acetate 500000 IE/g | 1 mg |
| 4. Vitamin E acetate 50% | 10 mg |
| 5. Vitamin D3 100000 IE/g | 1 mg |
| 6. Coenzyme Q10 | 5 mg |
| 7. Kolidon 30 | 10 mg |
| 8. Hydroxypropylmethylcellulose | 60 mg |
| 9. Cellulose | 10 mg |
| 10. Magnesium stearate | 5 mg |
| Ingredients (C) | |
| Opadry (II) white Y-22-7719 | 25 mg |

Ingredients are dispensed according to the above formulation for a batch size of 2000 tablets.

To prepare granulate (A), ingredients (A) 1 to 6 are sieved through a sieve of mesh size #20 (850 microns), and blended homogeneously in a laboratory-scale drum blender. Ingredient (A) 7 is then sieved through a sieve of mesh size #30 (600 microns) into the powder mixture, and further blended for 1 minute.

To prepare granulate (B), ingredients (B) 1 to 9 are sieved through a sieve of mesh size #20, and blended homogenously in a laboratory-scale drum blender. Ingredient (B) 10 is then sieved through a sieve of mesh size #30 into the powder mixture, and further blended for 1 minute.

The granulates (A) and (B) are compressed into double-layer oblong tablets of 1060 mg each with a rotary tablet press. The hardness is approximately 200 kN.

The tablet may be film-coated in white to improve appearance with a commercial coating formulation such as Opadry (II) White Y-22-7719 (Colorcon, Inc.). Opadry (II) White Y-22-7719 colouring agent consists of titanium dioxide, polydextrose, hypromellose, triacetin and polyethylene glycol 8000. To prepare the coating suspension, Opadry (II) White Y-22-7719 is dispersed in water with a homogenizer at a concentration of 15% w/w, stirred for 45 minutes, and filtered to form a coating suspension. The tablets are coated with the suspension in a perforated bed coater until a weight gain of 25 mg per tablet is achieved.

Tablet formulations for other plant fibres or non-plant fibres (e.g. chitosan) with cyclodextrin may be prepared in a similar manner to methods described in Examples 7 and 8 above. In some cases, such as chitosan-cyclodextrin combinations (e.g. chitosan-gamma cyclodextrin), it may be preferable to include in the tablet a physical mixture of the fibre and cyclodextrin.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention claimed is:

1. A composition for reducing absorption of dietary fat, comprising
   (a) a dietary fibre preparation derived from a plant belonging to the genus *Opuntia*, and
   (b) at least one cyclodextrin, wherein:
      (i) the at least one cyclodextrin is present in a sufficient amount such that the fat-binding ability of the dietary fibre preparation is increased relative to a composition comprising the dietary fibre preparation but lacking the at least one cyclodextrin,
      (ii) the cyclodextrin is selected from the group consisting of alpha-cyclodextrin, beta-cyclodextrin, gamma-cyclodextrin and combinations of two or more thereof, and
      (iii) the weight ratio of dietary fibre and cyclodextrin is between 95:5 and 60:40.

2. The composition of claim 1, wherein the dietary fibre preparation is derived from a plant belonging to the family Cactaceae in which the Cactaceae plant belongs to the species *Opuntia ficus-indica*.

3. The composition of claim 1 wherein the dietary fibre preparation is derived from a plant belonging to the family Cactaceae in which the dietary fibre preparation is derived from cladodes of *Opuntia ficus-indica*.

4. The composition of claim 1 in which the weight ratio of the dietary fibre and cyclodextrin is between 85:15 and 65:35.

5. The composition of claim 1 further comprising a biologically-active agent for treating obesity.

6. The composition of claim 5 in which the biologically-active agent is selected from the group consisting of absorption-altering, appetite-altering and metabolism-altering agent or combination thereof.

7. The composition of claim 1 further comprising a biologically-active agent for treating hyperlipidaemia.

8. The composition of claim 7 in which the biologically-active agent is selected from the group consisting of cholesterol-lowering agents and combinations thereof.

9. The composition of claim 1 further comprising a nutrient ingredient selected from the group consisting of vitamins and minerals and combinations thereof.

10. A method of reducing weight gain, comprising the step of administering a composition of claim 1 to a subject in need of such treatment.

11. A method of treatment of obesity, comprising the step of administering a composition of claim 1 to a subject in need of such treatment.

12. A method of treatment of hyperlipidaemia, comprising the step of administering a composition of claim 1 to a subject in need of such treatment.

13. A method of increasing the fat-binding ability of a dietary fibre preparation o derived from a plant belonging to the genus *Opuntia*, the method comprising the step of subjecting the dietary fibre to a physical interaction with a cyclodextrin, wherein:
    (i) the at least one cyclodextrin is present in a sufficient amount such that the fat-binding ability of the dietary fibre preparation is increased relative to a composition comprising the dietary fibre preparation but lacking the at least one cyclodextrin,
    (ii) the cyclodextrin is selected from the group consisting of alpha-cyclodextrin, beta-cyclodextrin, gamma-cyclodextrin and combinations of two or more thereof, and
    (iii) the weight ratio of dietary fibre and cyclodextrin is between 95:5 and 60:40.

14. A method of increasing the fat-binding ability of a dietary fibre preparation derived from a plant belonging to the genus *Opuntia*, the method comprising the step of physically mixing the dietary fibre with a cyclodextrin to homogeneity, wherein:
    (i) the at least one cyclodextrin is present in a sufficient amount such that the fat-binding ability of the dietary fibre preparation is increased relative to a composition comprising the dietary fibre preparation but lacking the at least one cyclodextrin,
    (ii) the cyclodextrin is selected from the group consisting of alpha-cyclodextrin, beta-cyclodextrin, gamma-cyclodextrin and combinations of two or more thereof, and
    (iii) the weight ratio of dietary fibre and cyclodextrin is between 95:5 and 60:40.

15. The composition of claim 1, wherein the fat-binding ability of the dietary fibre preparation is increased by at least about 10% relative to the composition comprising the dietary fibre preparation but lacking the at least one cyclodextrin.

16. The composition of claim 1, wherein the dietary fibre comprises approximately equal proportions of insoluble fibre and soluble fibre.

* * * * *